US008951559B2

(12) United States Patent
De Rosa

(10) Patent No.: US 8,951,559 B2
(45) Date of Patent: Feb. 10, 2015

(54) NANO-STRUCTURED THIXOTROPIC INORGANIC PEELING GELS

(75) Inventor: Mario De Rosa, Naples (IT)

(73) Assignee: MSB S.R.L., Avellino (IT)

( * ) Notice: Subject to any disclaimer, the term of this patent is extended or adjusted under 35 U.S.C. 154(b) by 1712 days.

(21) Appl. No.: 11/795,853

(22) PCT Filed: Jan. 24, 2006

(86) PCT No.: PCT/EP2006/000568
§ 371 (c)(1),
(2), (4) Date: Jul. 25, 2008

(87) PCT Pub. No.: WO2006/077156
PCT Pub. Date: Jul. 27, 2006

(65) Prior Publication Data
US 2009/0196926 A1    Aug. 6, 2009

(30) Foreign Application Priority Data

Jan. 24, 2005   (IT) .............................. NA2005A0003

(51) Int. Cl.
| | |
|---|---|
| A61K 9/14 | (2006.01) |
| A61P 17/02 | (2006.01) |
| A61Q 19/00 | (2006.01) |
| A61K 8/25 | (2006.01) |
| A61K 8/36 | (2006.01) |
| A61K 8/365 | (2006.01) |
| A61Q 5/00 | (2006.01) |

(52) U.S. Cl.
CPC ................ *A61Q 19/007* (2013.01); *A61K 8/25* (2013.01); *A61K 8/36* (2013.01); *A61K 8/365* (2013.01); *A61Q 5/006* (2013.01); *A61Q 19/00* (2013.01); *A61K 2800/28* (2013.01)
USPC .......................................................... 424/484

(58) Field of Classification Search
None
See application file for complete search history.

(56) References Cited

U.S. PATENT DOCUMENTS

| | | | | |
|---|---|---|---|---|
| 4,105,783 | A | * | 8/1978 | Yu et al. ......................... 514/459 |
| 5,618,522 | A | * | 4/1997 | Kaleta et al. .................... 424/60 |
| 6,093,218 | A | * | 7/2000 | Hall et al. .......................... 8/137 |
| 2003/0206878 | A1 | | 11/2003 | Gott et al. ........................ 424/63 |

FOREIGN PATENT DOCUMENTS

| | | |
|---|---|---|
| GB | 1 372 701 | 11/1974 |
| WO | WO 01/17497 | 3/2001 |
| WO | WO 02/051360 | 7/2002 |
| WO | WO 03/045345 | 6/2003 |

OTHER PUBLICATIONS http://skinpeel4u.com/chemical-skin-peel/ accessed on May 11, 2011.*

Pray, Steven W. "Nonprescription Alpha-Hydroxy Acids". US Pharmacist. 2002; 27(5).*
Chemical Abstracts Service, Columbus, Ohio, US, Retrieved from STN Database Accession No. 127: 23543, Abstract and JP 09 087165 (Noevir, K.K.) (Mar. 1997).
Rendon et al., "Evidence and Considerations in the Application of Chemical Peels in Skin Disorders add Aesthetic Resurfacing", J Clin Aesthetic Dermatol., 3(7):32-43 (2010).
Landau, M., "Chemical Peels" Clinics in Dermatology 26:200-208 (2008).
Mantovani et al., "Objective assessment of the minimal irritant reaction induced by a 70% solution of glycolic acid", Skin Research and Technology 3:222-226 (1997).
U.S. Food and Drug Administration, "Alpha Hydroxy Acids for Skin Care", FDA Consumer—Mar.-Apr. 1998; Revised May 1999.
Glycolic acid—Wikipedia, the free encyclopedia.
Baker, D., "Alpha Hydroxy Acids in Cosmetics", www.y2khealthanddetox.com.
FDA U.S. Food and Drug Administration, Cosmetics—Alpha Hydroxy Acids in Cosmetics.
Somerset Cosmetic Company, "How to use Alpha-Hydroxy Acids in Cosmetics", www.makingcosmetics.com.
NTP Technical Report 524 on Photocarcinogenesis study of glycolic and salicylic acid, National Institute of Health publication No. 07.4472 Sep. 2007 (CAS Nos. 79-14-1 and 67-72-7) (2007).

* cited by examiner

*Primary Examiner* — Robert A Wax
*Assistant Examiner* — Danah Al-Awadi
(74) *Attorney, Agent, or Firm* — Silvia Salvadori, P.C.

(57) ABSTRACT

A composition, a method, and a kit are provided for chemical skin peeling, based on nano-structured thixotropic inorganic gels, which have a higher potency and are less irritant of the conventional peeling formulations. The gels of the invention can easily be applied on the skin, where they form a stable, uniform layer, that doesn't strain. The kit comprises by a defatting gel, different types of peeling gels and a neutralizing gel. The defatting gel is characterized by a markedly enhanced defatting capacity in comparison to the conventional products, because the sebum solubilized by the solvent is strongly adsorbed on the huge surface of the nano-structured material of the gel. The peeling gels are based on conventional peeling compounds, such as glycolic acid, trichloroacetic acid, pyruvic acid, salicylic acid, Jessner solution, but the presence of nano-structured material strongly increases the peeling effect, allowing the use of lower concentrations of peeling compound, with only minimal skin irritation for the user. The neutralizing gel is characterized by a color change that allows the operator to verify in real time the neutralization of the peeling agent on the treated skin surface. All the gels of the invention can be easily removed from the skin after the treatment. The thixotropic gels of the invention can be used in chemical skin peeling for the treatment of various cosmetic conditions and dermatological disorders, including dry skin, acne, dandruff, keratoses, age spots, wrinkles and disturbed keratinization.

15 Claims, No Drawings

NANO-STRUCTURED THIXOTROPIC INORGANIC PEELING GELS

FIELD OF THE INVENTION

The invention relates to nano-structured gels for dermatological use, particularly for peeling.

BACKGROUND OF THE INVENTION

It is known that aging causes the stratum corneum to begin to lose its ability to renew itself through desquamation; in fact, mature skin may take twice as along to be renewed as compared to young skin. Treatments that accelerate the desquamation process of the stratum corneum increase the rate at which new cells of epidermal tissues are formed.

To restore the skin's freshness and youthful appearance, periodically a deep cleansing of the facial skin is needed, to increase epidermal desquamation and to remove the oily particles excreted from the sebaceous glands located in the dermis. These oil glands continuously excrete and channel the sebum from the deep dermis to minute openings at the skin surface. The sebum has a tendency to solidify over the sebaceous orifice, resulting in the formation of hardened plaques favouring the development of acne, cysts, white and black heads.

Skin peels for the treatment of aged or damaged skin have been used by dermatologists for some time. It is known that the outer layers of human skin can be caused to peel by applying special chemical formulations, able to remove dead skin and to wound underlying living skin tissue. Treatment of skin using a chemical peeling agent is typically called "chemical peel". Chemical peels are performed with chemical peeling agents such as alpha- and beta-hydroxy acids, trichloroacetic acid, phenols, etc. The chemical peeling agent is applied to the skin as aqueous or organic solutions, at an appropriate concentration, for a suitable period. In the chemical peeling the surface dead cells must be either removed or penetrated by the chemical peeling agents that loosen the bonds between dead skin cells and underlying living tissue, stimulating the cells to form new collagen.

Result of the chemical skin peeling is that the underlying layers of skin, now exposed, are relatively free of age lines, superficial wrinkles, acne scarring, dryness, pigment spots, aging spots and acne lesions. In addition, the exposed skin tissue looks more youthful in part, because it is smoother and reflects light more readily, thus rendering a "healthy glow" appearance. Deep chemical peels may cause undesirable skin reactions, such as frosting (whitening due to the denaturation of superficial proteins), rash or redness, on the skin of the wearer. If the wearer has such skin reactions, he or she should immediately discontinue the treatment. In some cases, another agent should be applied to the skin to neutralize the peeling agent.

Chemical peeling can be done in varying degrees of depth, called light, superficial, medium, and deep peels. A light or superficial peel is superficial in effect and produces few or no undesirable side effects, while medium or deep chemical peels produce a moderate to severe wound to the skin, with pain and inflammation. Medium and deep peeling is accomplished by the application of high-concentration peeling agents, either in a single treatment session, or, at most, over a period of repetitive treatments over several days in a professional setting. Deep peeling usually produces redness lasting several days, a large and deep separation of dead skin, and the exposure of deep living skin tissue. The results of medium and deep peeling are not equivalent to the results of light or superficial peels or exfoliation.

Additional steps of the peeling process have been disclosed, such as: before the peeling, the skin is cleaned and degreased applying various chemical agents on the skin; to stop the peeling, the peeling agents are neutralized and/or removed; at the end of the peeling treatment the affected skin is treated topically with a moisturizer or other after-care preparations.

Chemical peels require application of the peeling agent to the skin at an appropriate concentration. Direct application of the chemical peeling agent to the skin has however many problems in conjunction with formulation and application strategy. It tends to produce uncovered portions of the skin or result in uneven applications of the peeling agent. To overcome these problems, the prior art describes the use of bandage pad or a similar patch. Conventional bandage pads designed to stay on the skin for chemical peels have a backing made of fabric with a chemical peeling agent applied thereto.

The prior art doesn't provide univocal data for standardization of the peeling process. Generally, a dermatologist, aesthetician or cosmetologist does not apply skin peeling agents in a uniform way with respect to: the preparatory degreasing, a critical area of variability in the effectiveness and depth of skin penetration achieved by the skin peeling agents; the type of ingredients used and their concentrations; the duration of skin contact with the peeling agents; the degree of abrasiveness employed in the course of treatment; the post-treatment for affected skin.

Different types of peeling treatments or protocols have been described. Various attempts have been made to utilize alpha-hydroxy acids, such as glycolic acid and other compounds in skin care products, as noted in U.S. Pat. Nos. 3,879,537, 3,920,835, 3,984,566, 3,988,470, 4,021,572, 4,105,783, 4,197,316, 4,234,599, 4,246,261, 4,363,815, 4,380,549 and 4,363,815. The peeling agents described in these patents, in addition to the glycolic acid, include citric, glucuronic, alpha-hydroxybutyric, alpha-hydroxy-isobutyric, lactic, malic, mandelic, mucic, pyruvic, galacturonic, beta-phenyllactic, beta-phenylpyruvic, beta-hydroxybutyric, saccharic, tartaric, tartronic acids, glucuronolactone, gluconolactone, methyl pyruvate, ethyl pyruvate. However, glycolic acid is more effective in treating skin conditions, because of its activity in relation to the removal of dead skin layers and moisturizing and on treating live skin. In fact, glycolic acid penetrates the dermal layers better than other alpha hydroxy acids and peeling agents, thanks to its relatively smaller molecular size. Furthermore, glycolic acid acts better at peeling and/or exfoliating skin when used synergistically in combination with relatively low concentrations of acetone. Glycolic acid has been specifically described as an agent to loosen bonds between dead and live skin cell layers, as noted in M. Murad, "A Primer on Glycolic Acid," March/April, 1993, Dermascope, Dallas, Tex. 75202. However, the use of glycolic acid has been criticized in U.S. Pat. No. 4,294,852, which alleges that the use of certain alcohols in combination with alpha-hydroxy acids permits their use in significantly lower concentration to achieve the same result.

U.S. Pat. Nos. 4,874,361 and 5,166,176 disclose the use of tricholoroacetic acid (TCA) as peeling agent in association with surfactants and emulsifiers which are spread over the affected skin area. The covered skin area is then subjected to ultraviolet radiation. The resulting peel yields a new layer of vibrant, evenly coloured, healthy skin, usually with only a single application.

U.S. Pat. No. 4,608,370 discloses the use of lactic acid, salicylic acid, alcohol and resorcinol administered once in a single application, where the intended effect is expected to occur over a week period for removal of dead skin in what is referred to as "peeling" in a non-irritating manner.

U.S. Pat. No. 5,164,413 teaches the treatment of acne with formulations comprising resorcinol, lactic acid, salicylic acid and ethanol. This treatment has a controlled irritation, so that blemished skin dies after minor irritation and is replaced by healthy, fresh skin in the process known as exfoliation.

Other related preparations for skin treatment include U.S. Pat. No. 4,035,513, U.S. Pat. No. 4,124,720, U.S. Pat. No. 4,195,077, U.S. Pat. No. 4,287,214, U.S. Pat. No. 4,505,925, U.S. Pat. No. 4,695,452, U.S. Pat. No. 4,824,865, U.S. Pat. No. 4,931,591, U.S. Pat. No. 5,110,603, U.S. Pat. No. 5,720,390, U.S. Pat. No. 5,962,4411, U.S. Pat. No. 5,730,991, U.S. Pat. No. 5,728,390, U.S. Pat. No. 5,863,546, U.S. Pat. No. 6,169,110, U.S. Pat. No. 6,521,271, US 20020192253, US 20040039323 and US 20040067243.

Cosmetic applicator pads and/or medicated cleansing pads have been described in use with salicylic acid and alcohol, as noted in U.S. Pat. No. 4,891,228. Other patents relating to cosmetic or medicated applicator pads include U.S. Pat. Nos. 3,706,595 and RE 28,957; U.S. Pat. No. 3,778,341; U.S. Pat. No. 4,341,213; U.S. Pat. No. 4,719,226; U.S. Pat. No. 4,738,848.

Moreover, U.S. Pat. No. 4,514,385 discloses salicylic acid in an anti-acne aqueous gel delivered in a polymer vehicle and U.S. Pat. No. 4,830,854 teaches the use of salicylic acid in a pad for desquamation of skin, epidermal hydration, along with diffuse loosening of a foreign body embedded in the skin.

DESCRIPTION OF THE INVENTION

The invention discloses a kit for chemical skin peeling comprising nano-structured thixotropic inorganic gels, which have a higher potency and are less irritant of the conventional peeling formulations. The gels of the invention can easily be applied on the skin, where they form a stable, uniform layer, that doesn't strain.

The defatting gel is characterized by a markedly enhanced defatting capacity in comparison to the conventional products, because the sebum solubilized by the solvent is strongly adsorbed on the enormous surface of the nano-structured material present in the gel. The peeling gels are based on conventional peeling compounds, such as glycolic acid, trichloroacetic acid, pyruvic acid, salicylic acid, Jessner solution, but the presence of nanostructured material strongly increases the peeling effect, allowing the use of a lower concentration of peeling compound, with only minimal skin irritation for the user. The neutralizing gel is characterized by a colour change that allows the operator to verify in real time the neutralization of the peeling agent on the treated skin surface. All the gels of the invention can be easily removed by the skin after the treatment.

DETAILED DESCRIPTION OF THE INVENTION

The kit for skin peeling of the invention comprises:
a) a defatting or detergent thixotropic gel consisting of organic solvents and/or amphiphilic or a polar surfactant;
b) a peeling thixotropic gel comprising a peeling agent;
c) a neutralizing thixotropic gel consisting of a solution of an alkali carbonate or bicarbonate and a pH indicator having a pKi ranging from 2 to 8.

The thixotropic properties are imparted to gels a), b) and c) by means of a suitable nano-structured inorganic matrix preferably selected from nanoparticles of silica, aluminium dioxide or titanium dioxide. Silica, particularly fumed silica having a density of 0.1 g/ml, average particle size from 70 to 40 nm and a surface from 400 to 50 $m^2/g$, is preferred.

Fumed silica is a synthetic, amorphous, colloidal silicon dioxide. It is produced by the vapour hydrolysis of chlorosilanes, such as silicon tetrachloride, in a hydrogen-oxygen flame at 1800° C.

In the combustion process, molten spheres of amorphous silica are formed. Fumed silica is a white fluffy powder, consisting of spherically shaper primary particles, ranging in average from 7 to 40 nanometers in diameter, with a surface area of 400 to 50 square meters per gram. Primary particles do not exist in isolation; they form aggregates and agglomerates. Technical properties of the fumed silica are not just determined by the primary particles, but also by the agglomerate size distribution. The fumed silica does not have a clearly defined agglomerate size. The particle size distribution becomes wider as the average primary particle size increases and the tendency to form agglomerates is reduced.

Many kinds of hydrophilic and hydrophobic fumed silica are produced by Degussa with the trade mark Aerosil (Degussa AG Rodenbacher Chaussee 4 D-63403 Hanau-Wolfgang, Germany). In particular hydrophobic fumed silica is obtained from fumed silica by reacting the silanol groups with various silanes and silazanes.

Examples of the preferred hydrophilic fumed silica are Aerosil 90, Aerosil 130, Aerosil 150, Aerosil 200, Aerosil 300, and Aerosil 380 with increasing specific surface area and thickening and thixotropic effect. Examples of hydrophobic fumed silica are Aerosil R 812, Aerosil R 816 and Aerosil R 972.

When fumed silica is dispersed in a liquid, the silanol groups of the surface of different particles can interact by hydrogen bond with each other, to form connecting bridges. A three dimensional structure develops, which has a thickening effect. This structure can be broken down again by subjecting the system to mechanical stress, either through stirring or shaking. The extent of the break down depends on the type and duration of the mechanical stress. The thickened system thereby regains its mobility. Hydrophilic fumed silica gel has a less pronounced thickening effect in polar liquids. In these systems, surface modified fumed silica shows a remarkable rheological effectiveness due to the formation of three-dimensional solvate- or adsorbate structures.

Fumed silica meets all the requirements for "Colloidal Silica Dioxide" as described in the USP-National Formulary. Preferred fumed silica Aerosil is pure commercially available amorphous silica. It is at least 99.8% by weight silicon dioxide on an ignited weight basis. The defatting gel a) may contain a solvent selected from acetone, alcohols such as ethanol or butandiol, ethers. In this case, the nano-structured inorganic matrix is hydrophobic.

Alternatively, the gel a) may contain a detergent gel containing a amphiphilic or apolar surfactant and in this case the nano-structured inorganic matrix is hydrophilic.

Suitable peeling agents contained in gel b) include glycolic acid, citric acid, glucuronic acid, alpha-hydroxybutyric acid, lactic acid, malic acid, mandelic acid, mucic acid, pyruvic acid, galacturonic acid, beta-phenyl-lactic acid, beta-phenyl pyruvic acid, beta-hydroxybutyric acid, saccharic acid, tartaric acid, tartronic acid, glucuronolactone, gluconolactone, trichloroacetic acid.

Said peeling agents are formulated with an hydrophilic nano-structured inorganic matrix.

Other peeling agents which may be used according to the invention include resveratrol, resorcinol, phenol, salicylic acid, Jessner solution, methyl pyruvate, ethyl pyruvate and in this case the nano-structured inorganic matrix is hydrophobic.

Typically, an hydrophobic nano-structured inorganic matrix is silica having dimethylsilyl and trimethylsilyl groups.

The nano-structured inorganic matrix is usually present in the gels a), b) or c) in amounts from 1 to 30% w/w.

The gel a) comprises from 1 to 20% of a surfactant in addition to de-sensitizing and lenitive agents.

The gel b) contains from 70 to 99% of an aqueous or organic solution of the peeling agent.

A preferred neutralizing gel c) comprises phenol red, sodium bicarbonate and propylene glycol.

The gels of the invention have the following advantages over the prior art:

1) The thixotropic property, i.e. a particular rheological condition, for which in absence of blending, the gel becomes solid, while the simple blending during the application on the skin makes it fluid. The thixotropic behaviour allows applications on the skin, with a brush or a spatula, according to the experience of the dermatologist. The use of the thixotropic gels of the invention is of high effectiveness in the peeling treatments, because it allows a homogeneous and visible distribution of the product on the skin, avoiding drippings and therefore the need for the operator to protect the zones not to be treated. At the end of the peeling, the residual product can be easily removed with a spatula.

2) The controlled release—The nano-structures present in the gel have a very high specific surface: 1 g of nano-particles has, in fact, a surface of about 300 m². In the gel of the invention the surface properties suitably control the mass flow between the gelled matrix and the skin. The active principles are adsorbed on the very large surface of the nano-structured material present in the gels and are released on the skin homogeneously and continuously during the treatment. This avoids inaestheticisms due to a non-homogeneous peeling.

3) The facilitated penetration—the nano-particles, about 10.000 times smaller than 1 mm, easily penetrate the treated surface, releasing the active principle. This makes the treatment more effective and homogeneous in comparison with traditional products having the same concentration.

4) The depurating action—The nano-particles of the gel adsorb the impurities of the treated skin, facilitating the penetration of the active compounds and the removal of impurities and dead cells. This behaviour allows to obtain homogeneous and effective skin peelings.

5) The chemical stability—One of the most remarkable problems of the peeling formulates are their high acidity, that degrades the rheological components. The high chemical stability of the used nano-structured matrices guarantee high stability of the claimed gels, that maintain their characteristics unchanged in time, also under severe conditions of maintenance.

As far as the thixotropic defatting gel is concerned, it has also been found that keeping the concentrations of the peeling agents constant, and varying the type and concentration of the defatting agent, a change in the peeling rate may be obtained. This points out that the process of skin defatting plays a critical role in the effectiveness and in the quality of the peeling. An incomplete and not homogeneous defatting will determine an insufficiently deep and not homogeneous peeling.

The preferred product for the defatting gel is Aerosil R 812 methylated fumed silica (Degussa).

Table 1 compares the oil absorption potential of different compounds and shows the superior properties of the Aerosil R812 methylated fumed silica. Squalene, the principal oil found in sebum, is used as the oil to be absorbed.

U.S. Pat. No. 4,536,399 reports that hydrophilic fumed silica possesses oil-absorptive properties useful for treatment of oily skin. However, this is completely different from the defatting gels of the present invention, because said patent merely discloses lipophilic particles in organic solvent and does not disclose a thixotropic gel, using hydrophilic fumed silica 1-10% in a in an oil-in-water emulsion carrier, said carrier consisting of 1-4% of a thickening agent/emollient selected from the group consisting of cetyl alcohol, stearic acid and glycerol monostearate, 0.25-1.5% sodium lauryl sulfate emulsifier, and water q.s. 100%.

TABLE 1

Oil absorption capacity of various ingredients as determined by ASTM Rubout method*

| | |
|---|---|
| Aluminium hydroxide | 0.53 |
| Microfine bentonite | 0.51 |
| Syloid 244 silica precipitated | 2.75 |
| Aerosil 300 hydrophilic silica fumed (Degussa) | 4.20 |
| Aerosil R812 hydrophobic methylated silica fumed (Degussa) | 6.50 |

*Results expressed as ratio g of oil absorbed per g of sample.

As already mentioned, peeling gels based on hydro-soluble chemical compounds, such as glycolic or trichloroacetic acid, are prepared using thixotropic hydrophilic nano-structured materials, preferably Aerosil 300 or 380 (Degussa) in concentrations from 0.1 to 30% w/w, preferably from 2 to 10% w/w. Peeling gels based on chemical compounds soluble in organic solvents, such as salicylic acid or the Jessner formulation, are preferably prepared using thixotropic hydrophobic nano-structured material, such as Aerosil R812 or R816 (Degussa) in concentrations from 0.1 to 30% w/w, from 2 to 10% w/w. The presence of thixotropic nano-structured material not only confers a thixotropic behaviour to the peeling gel, but the elevated surface/mass ratio of the nano-structured particles favours the elimination of the cutaneous impurities. In fact, the nano-structured particles behave as an efficient lubricating system, which favours the exfoliation process of the dead cells of the superficial layers of the derma. The nano-structured particles have dimensions that fit the intracellular spaces of the skin; they deeply enter during the treatment, acting as a slow release system of the peeling chemicals. The result is a more efficient and less irritant peeling in comparison with conventional solutions of the same concentration. Using the gels of the invention, the dermatologist can employ lower concentrations of the chemical peeling compound, getting the best results with a modest cutaneous irritation, without traumas for the patient.

The neutralizing nano-structured thixotropic gel c), under conditions of persistent cutaneous acidity, becomes pale yellow and releases gas, whereas, when the pH returns to the neutrality on the skin, the gel maintains its pink colour. At the end of the neutralizing treatment the gel is removed with a spatula, gauze or a cellulosic fabric pad before cleansing the skin. The neutralizing gel usually consists of a water solution of sodium bicarbonate or carbonate ranging from 1% w/w to saturation, in preference from 10 to 20% w/w, containing from 1 to 30% w/w of an alcohol, and a pH indicator that have a pKi ranging from 2 to 8, in preference red phenol.

The following examples disclose the invention in more detail.

Example 1

Thixotropic nano-structured defatting gel—Formulation (% w/w): acetone from 5 to 50, ethanol from 5 to 50, 1,4-butandiol from 5 to 50, Aerosil R 812 from 1 to 30.

The formulation is made as follows: 1) Mix together the solvent; 2) add Aerosil R 812 and mix up to have a fluid, transparent, homogeneous gel. In absence of blending, the thixotropic gel becomes solid, while the simple blending during the application on the skin makes it fluid. The gel preparation stored at room temperature is stable for several years.

A treatment with the thixotropic nano-structured defatting gel is recommended for the preparation of the skin for the peeling. The nano-particles of the gel adsorb the lipid impurities of the treated skin on their huge surface, making the peeling treatment more homogeneous and facilitating a deeper penetration of peeling compounds.

The thixotropic behaviour of the gel allows applications on the skin, with a brush or a spatula, according to the experience of the dermatologist. After few minutes from the application the material can be easily removed with a spatula or a fabric pad.

Example 2

Thixotropic nano-structured peeling gel of salicylic acid—Formulation (% w/w): salicylic acid from 1 to 30, Aerosil R 812 from 1 to 30, ethanol up to 100. The formulation is made as follows: 1) solubilize salicylic acid in the solvent; 2) add Aerosil R812 and mix up to have a fluid, transparent, homogeneous gel. In absence of blending, the thixotropic gel becomes solid, while the simple blending during the application on the skin makes it fluid. The gel preparation stored at room temperature is stable for several years. The thixotropic behaviour of the gel allows applications on the skin, with a brush or a spatula.

This formulation is more effective and enables dermatologist to use lower concentrations of salicylic acid with respect to conventional formulations of the same agent. The peeling action is stopped by neutralizing the acidity with the gel c).

Example 3

Thixotropic nano-structured peeling gel of pyruvic acid—Formulation (% w/w): pyruvic acid from 1 to 80, Aerosil 300 from 1 to 30, water up to 100. The formulation is made as follows: 1) solubilize pyruvic acid in the solvent; 2) add Aerosil 300 and mix up to have a fluid, transparent, homogeneous gel. In absence of blending, the thixotropic gel becomes solid, while the simple blending during the application on the skin makes it fluid. The gel preparation stored at room temperature is stable for several years. The thixotropic behaviour of the gel allows applications on the skin, with a brush or a spatula.

This formulation is more effective and enables the dermatologist to use lower concentrations of pyruvic acid with respect to conventional formulations of the same agent. The peeling action is stopped by neutralizing the acidity with the gel c).

Example 4

Thixotropic nano-structured peeling gel of glycolic acid—Formulation (% w/w): glycolic acid from 1 to 80, Aerosil 300 from 1 to 30, water up to 100. The formulation is made as follows: 1) solubilize glycolic acid in water; 2) add Aerosil 300 and mix up to have a fluid, transparent, homogeneous gel. In absence of blending, the thixotropic gel becomes as a solid, while the simple blending during the application on the skin makes it fluid. The gel preparation stored at room temperature is stable for several years. The thixotropic behaviour of the gel allows applications on the skin, with a brush or a spatula.

This formulation is more effective and enables the dermatologist to use lower concentrations of glycolic acid with respect to conventional formulations of the same agent. The peeling action is stopped by neutralizing the acidity with the gel c).

Example 5

Thixotropic nano-structured peeling gel of trichloroacetic acid (TCA)—Formulation (% w/w): trichloroacetic acid from 1 to 80, Aerosil 300 from 1 to 30, water up to 100. The formulation is made as follows: 1) solubilize trichloroacetic acid in water; 2) add Aerosil 300 and mix up to have a fluid, transparent, homogeneous gel. In absence of blending, the thixotropic gel becomes solid, while the simple blending during the application on the skin makes it fluid. The gel preparation stored at room temperature is stable for several years. The thixotropic behaviour of the gel allows applications on the skin, with a brush or a spatula.

This formulation is more effective and enables the dermatologist to use lower concentrations of TCA acid with respect to conventional formulations of the same agent. The peeling action is stopped by neutralizing the acidity with the gel c).

Example 6

Thixotropic nano-structured peeling gel of Jessner solution—Formulation (% w/w): salicylic acid 14, lactic acid 14, resorcinol 14, Aerosil R972 from 1 to 30, ethanol up to 100. The formulation is made as follows: 1) solubilize salicylic, lactic acid, and resorcinol in ethanol; 2) add Aerosil R972 and mix up to have a fluid, transparent, homogeneous gel. In absence of blending, the thixotropic gel becomes solid, while the simple blending during the application on the skin makes it fluid. The gel preparation stored at room temperature is stable for several years. The thixotropic behaviour of the gel allows applications on the skin, with a brush or a spatula.

This formulation is more effective and enables the dermatologist to use lower concentrations of Jessner solution with respect to conventional formulations of the same agent. The peeling action is stopped by neutralizing the acidity with the gel c).

Example 7

Thixotropic nano-structured neutralizing gel—Formulation (% w/w): sodium bicarbonate from 10 to 20, Aerosil 200 from 1 to 30, propylene glycol from 2 to 20, red phenol from 0.01 to 1.0 water up to 100. The formulation is made as follows: 1) solubilize sodium bicarbonate, propylene glycol, and red phenol in water; 2) add Aerosil 200 and mix up to have a fluid, transparent, red coloured, homogeneous gel. In absence of blending, the thixotropic gel becomes solid, while the simple blending during the application on the skin makes it fluid. The gel preparation stored at room temperature is stable for several years. The thixotropic behaviour of the gel allows applications on the skin, with a brush or a spatula.

When the gel is applied on the skin at the end of the peeling, a change in colour shows the completion of neutralization. Initially, in conditions of persistent cutaneous acidity, the gel is pale yellow and releases gas. When the pH returns to the neutrality, the gel maintains its pink colour. At the end of the treatment the gel can be easily removed with a spatula, before cleansing the face.

Example 8

Clinical tests—5 dermatologists treated 10 volunteers each, representing a cross section of women 25 to 60 years old.

Each dermatologist used a different peeling compound (table 2) and each volunteer was treated on the right side of the face with a conventional peeling kit and on the left side with the kit of the invention. With the exception of Jessner solution, the thyxotropic gels had lower concentrations of the chemical peeling agent, in view of their higher activity in comparison with the equivalent conventional solutions.

The effectiveness of the two treatments was evaluated by the dermatologists and by the volunteers using the following parameters: the dermatologist evaluated: 1) easiness of application; 2) efficacy of degreasing treatment; 3) efficacy of peeling; 4) easiness of use of neutralizing gel; 5) pain induced by treatment; 6) quality of treatment; 7) overall convenience.

The volunteers were asked to evaluate: 1) pain induced by treatments; 2) quality of treatments. The volunteers were treated simultaneously with the conventional products and with the kit of the invention, the sequence of two treatments was random; 20 days later the volunteers filled in the questionnaires whereas dermatologists evaluated the parameters reported above for the 10 volunteers treated.

TABLE 2

Experimental protocol

| Dermatologist Code | Treatment* | |
|---|---|---|
| | conventional peeling | peeling with thixotropic gels of the invention |
| 1 | salicylic acid 20% | salicylic thixotropic gel 15% |
| 2 | glycolic acid 70% | glycolic acid thixotropic gel 60% |
| 3 | pyruvic gel 50% | pyruvic acid thixotropic gel 40% |
| 4 | trichloroacetic acid 50% | trichloroacetic acid thixotropic gel 40% |
| 5 | Jessner solution | Jessner solution thixotropic gel |

*each dermatologist used, in the conventional peeling treatment, conventional degreasing/defatting and neutralizing solutions and in the treatment with thixotropic peeling gel, degreasing/defatting and neutralizing thixotropic gels of the invention.

The following conclusions were drawn from dermatologists: 100% showed a strong preference for thixotropic gels of the invention, considered easier to use, because the products form a homogeneous layer on the skin, can be easily applied both with a brush or with a spatula, don't drip, are well evident on the treated area, do not require the protection of the areas not to be treated, the residual product can be easily removed from the skin with a spatula, gauze or a cellulosic fabric pad; 100% of the dermatologists showed a strong preference for thixotropic degreasing/defatting gel of the invention, considered easy to use and with an optimal degreasing/defatting and cleaning effect on the skin; 100% of dermatologists clearly preferred the peeling kit of the invention; 100% of dermatologists considered the neutralizing gel of the invention more effective, simple to use and reliable; 80% of the dermatologists pointed out that the volunteers considered the treatment with the kit of the invention less painful; 100% of the dermatologists pointed out that the products of the invention gave a peeling of better quality.

The following conclusions were drawn from volunteers: 84% considered the treatment with the products of the invention less painful, 16% didn't notice differences among the two treatments; 80% considered the peeling obtained with the products of the invention more effective, while 20% didn't notice differences among the two treatments.

The invention claimed is:

1. A kit for skin peeling comprising three separate compositions comprising:
    a) a defatting or detergent thixotropic gel comprising organic solvents and/or amphiphilic or apolar surfactant;
    b) a peeling thixotropic gel comprising a peeling agent; and
    c) a neutralizing thixotropic gel comprising a solution of an alkali carbonate or bicarbonate and a pH indicator having a pKi ranging from 2 to 8;
    wherein the thixotropic gels a), b) and c) comprise a nano-structured matrix of silica, aluminum, dioxide or titanium dioxide, in amounts from 1 to 30% w/w.

2. The kit according to claim 1 wherein the nano-structured inorganic matrix is silica.

3. The kit according to claim 2, wherein the nano-structured inorganic matrix is fumed silica having a density of 0.1 g/ml, average particle size from 70 to 40 nm and a surface from 400 to 50 m$^2$/g.

4. The kit according to claim 1 wherein the kit comprises a defatting gel containing a solvent selected from acetone, alcohols, ethers.

5. The kit according to claim 4, wherein the solvent is acetone, ethanol, butandiol or mixtures thereof.

6. The kit according to claim 4 wherein the nano-structured inorganic matrix is hydrophobic.

7. The kit according to claim 1 wherein the kit comprises a detergent gel containing a amphiphilic or apolar surfactant and the nano-structured inorganic matrix is hydrophilic.

8. The kit according to claim 1 wherein the peeling agent is selected from glycolic acid, citric acid, glucuronic acid, alpha-hydroxybutyric acid, lactic acid, malic acid, mandelic acid, mucic acid, pyruvic acid, galacturonic acid, beta-phenyl-lactic acid, beta-phenyl pyruvic acid, beta-hydroxybutyric acid, saccharic acid, tartaric acid, tartronic acid, glucuronolactone, gluconolactone and trichloroacetic acid.

9. The kit according to claim 8 wherein the nano-structured inorganic matrix is hydrophilic.

10. The kit according to claim 1 wherein the peeling agent is resveratrol, resorcinol, phenol, salicylic acid, Jessner solute, methyl pyruvate, ethyl pyruvate.

11. The kit according to claim 10 wherein the nano-structured inorganic matrix is hydrophobic.

12. The kit according to claim 11 wherein the nano-structured inorganic matrix is silica having dimethylsilyl and trimethylsiyl groups.

13. The kit according to claim 1 wherein the gel a) comprises from 1 to 20% of a surfactant in addition to de-sensitizing and lenitive agents.

14. The kit according to claim 1 wherein the gel b) contains from 70 to 99% of an aqueous or organic solution of the peeling agent.

15. The kit according to claim 1 wherein the neutralizing gel comprises the pH indicator of phenol red, the bicarbonate of sodium bicarbonate and propylene glycol.

* * * * *

UNITED STATES PATENT AND TRADEMARK OFFICE
CERTIFICATE OF CORRECTION

| | | |
|---|---|---|
| PATENT NO. | : 8,951,559 B2 | Page 1 of 1 |
| APPLICATION NO. | : 11/795853 | |
| DATED | : February 10, 2015 | |
| INVENTOR(S) | : M. De Rosa | |

It is certified that error appears in the above-identified patent and that said Letters Patent is hereby corrected as shown below:

On the Title Page

Column 1, item (73) Assignee

MSB S.R.L., Avellino (IT) should read "MBS S.R.L., Avellino (IT)"

Signed and Sealed this
Eighteenth Day of August, 2015

Michelle K. Lee
*Director of the United States Patent and Trademark Office*